Figure 1:
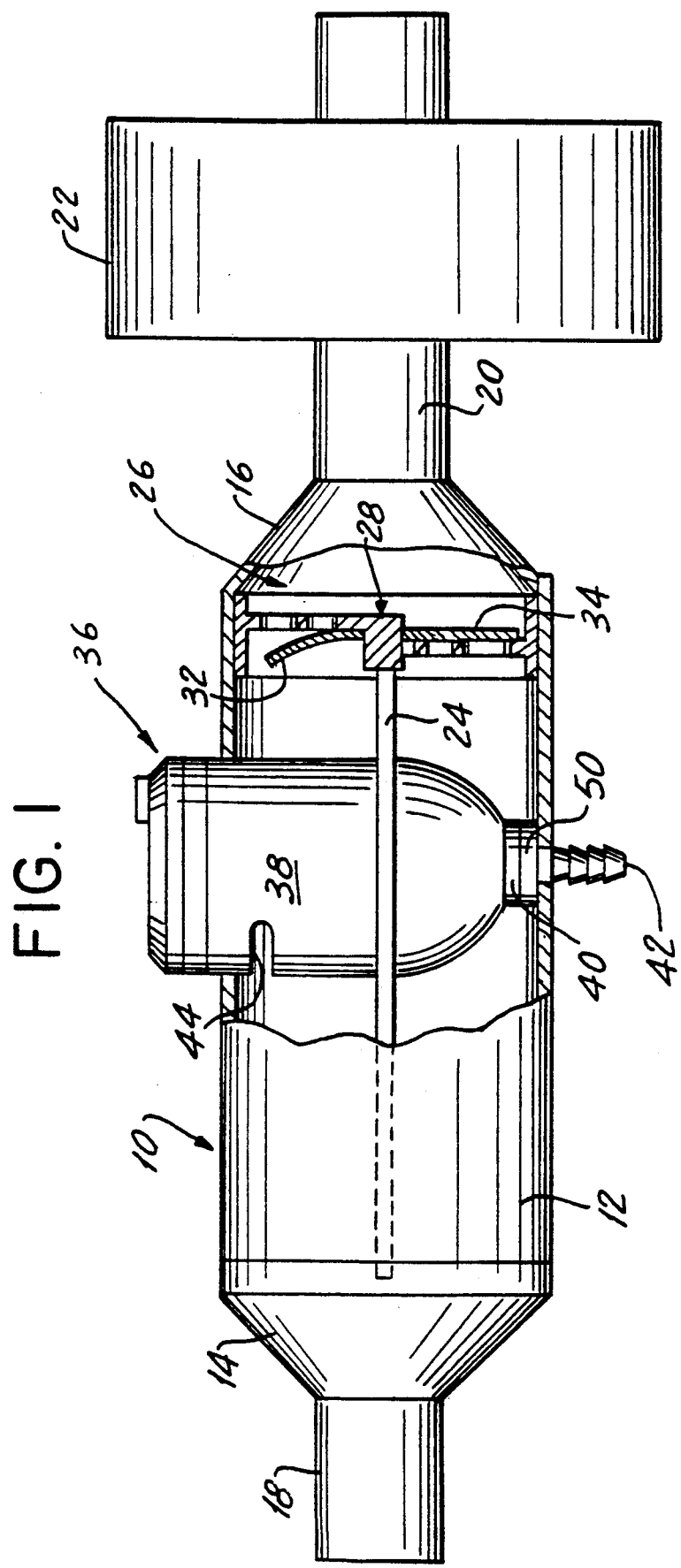
Figure 2:
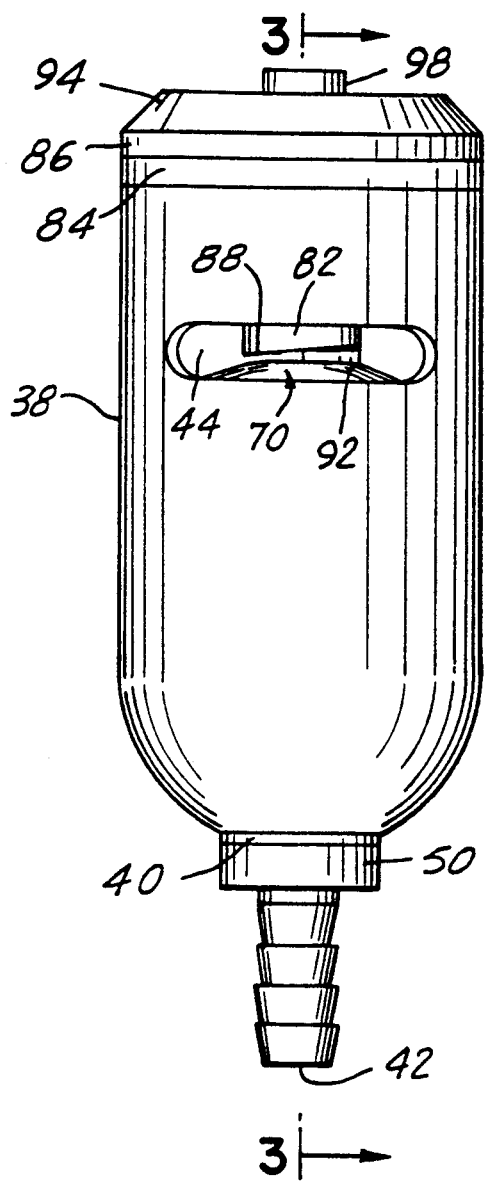

United States Patent [19]

Small, Jr.

[11] Patent Number: 5,301,663
[45] Date of Patent: * Apr. 12, 1994

[54] AEROSOL DELIVERY SYSTEM

[75] Inventor: John C. Small, Jr., Bethlehem, Conn.

[73] Assignee: Healthscan Products, Inc., Cedar Grove, N.J.

[*] Notice: The portion of the term of this patent subsequent to Nov. 24, 2009 has been disclaimed.

[21] Appl. No.: 978,631

[22] Filed: Nov. 19, 1992

Related U.S. Application Data

[63] Continuation-in-part of Ser. No. 731,037, Jul. 16, 1991, Pat. No. 5,165,392.

[51] Int. Cl.$^5$ ............................................. A61M 11/00
[52] U.S. Cl. ............................ 128/200.18; 128/200.21; 137/512.4
[58] Field of Search ...................... 128/200.14, 200.18, 128/200.21, 911, 205.24; 239/338; 251/321; 137/512.15, 512.4

[56] References Cited

U.S. PATENT DOCUMENTS

| | | | |
|---|---|---|---|
| 2,723,055 | 11/1955 | Beard, Jr. | 251/321 |
| 2,826,454 | 3/1958 | Coanda | 128/200.18 |
| 3,826,255 | 7/1974 | Havstad et al. | 128/200.21 |
| 4,333,450 | 6/1982 | Lester | 128/200.18 |
| 4,437,490 | 3/1984 | Demers et al. | 137/512.4 |
| 4,529,003 | 7/1985 | Iannuzzelli et al. | 128/200.14 |
| 4,792,097 | 12/1988 | Kremer, Jr. et al. | 239/338 |
| 4,796,614 | 1/1989 | Nowacki et al. | 128/200.14 |
| 4,907,581 | 3/1990 | King | 128/200.18 |
| 4,976,284 | 12/1990 | Hovarter | 137/512.4 |
| 5,054,477 | 10/1991 | Terada et al. | 128/200.14 |
| 5,165,392 | 11/1992 | Small, Jr. | 128/200.18 |

Primary Examiner—Edgar S. Burr
Assistant Examiner—Stephen R. Funk
Attorney, Agent, or Firm—Schweitzer Cornman & Gross

[57] ABSTRACT

An improved aerosol delivery system utilizes a pair of horizontally-extending passageways terminating in common opposed ends, the first end being mouthpiece-adjustable, the second end being coupled to the atmosphere. A dual action valve, utilizing a single diaphragm element, provides for opposed one-way air flow through the passageways. A nebulizer is mounted transversely through the passageways, and outputs into the passageway allowing inspiratory flow to the user. A combination adjustment knob/fill port is located at the top of the nebulizer, which extends upwardly above the passageways. The knob is coupled to a valve which meters the liquid to be aspirated which may be aligned with an aperture in the top of the nebulizer for filling purposes. During normal use the apertures are out of alignment, closing the fill port.

15 Claims, 4 Drawing Sheets

AEROSOL DELIVERY SYSTEM

This application is a continuation-in-part of U.S. Ser. No. 731,037, filed Jul. 16, 1991, now U.S. Pat. No. 5,165,392.

FIELD OF THE INVENTION

The present invention relates to aerosol delivery systems, and more particularly to an improved aerosol delivery system in the form of a nebulizer of compact design contained in a unique, compact manifold system.

BACKGROUND OF THE INVENTION

Nebulizers are well known. They are devices for producing a mist or fog of a fluid, which may be a medication. Typical uses for such devices are in connection with inhalation therapy. They may also be used for inhalation of a radioactive pharmaceutical for use in ventilation scans and in other nuclear medicine applications.

The present application's parent application, Ser. No. 731,037, now U.S. Pat. No. 5,165,392, discloses a nebulizer of compact design which is adapted to provide accurate metering of the liquid to be nebulized. Further disclosed in that application is an innovative valve system which controls the passage of both ambient air, which serves as the carrier for the nebulized fluid, through the delivery system to the patient as well as the passage of expired air from the patient in a manner which bypasses the nebulizer.

The present invention provides additional novel improvements to the nebulizer delivery device of the aforementioned application. The present invention provides further enhanced liquid metering and incorporates a valve design which is of simplified unique construction, which results in a nebulizer unit having further improved performance over conventional units.

It is accordingly an object of this invention to provide a more efficient and effective aerosol delivery system of compact design.

It is a further object of the invention to provide a nebulizer which provides more accurate dosages than heretofore possible.

It is another object of the invention to provide a nebulizer which provides for more comfortable delivery of irritating medication.

It is a still further object of the invention to provide an aerosol delivery system which requires less medication to achieve the same delivery to a patient.

Another object of the invention is to provide a nebulizer which causes less aeration and foaming of the medication than heretofore possible.

It is an additional object of the invention to provide a nebulizer having simple component designs which facilitate component manufacture by inexpensive injection molding techniques. Yet another object of the present invention is the provision of a novel and efficient two-way valve which may be incorporated into nebulizers and other devices having opposed fluid flows.

SUMMARY OF THE INVENTION

The present invention incorporates a manifold system having a unitary hollow body with a first opening to accommodate the ingress of fresh air and the egress of exhaled air, and a second opening to accommodate the egress of modified fresh air and the ingress of exhaled air. The two openings are interconnected by each of two vertically juxtaposed chambers with horizontally parallel axes in the hollow body. One chamber is valved to pass fresh air from the first opening to the second opening for inhalation by the user, and the second chamber is valved to pass user-exhaled air from the second opening to the first opening and out of the manifold at a distance from the user.

The manifold seats a nebulizer having an outlet in the downstream side of the first chamber to pass mist developed by the nebulizer therethrough into the first chamber. Thus, fresh air to be inhaled by the user is modified by inclusion of the mist developed by the nebulizer as the air passes through the first chamber and past the nebulizer. Air exhaled by the user patient will pass through the second chamber, without significant obstruction by the nebulizer.

The nebulizer is of an improved design producing an aerosol of unusually fine particles. In addition, it is precisely incrementally adjustable to vary the number of fine particles being produced. It also allows for improved convenience in filling with the liquid, typically a medication, to be nebulized.

The nebulizer includes a hollow stem adapted to pass a jet of pressurized gas, such as air or oxygen, out of its upper end or surface. The stem is mounted within the lower portion of the nebulizer, which is adapted to hold the liquid to be nebulized or mixed with the gas, and is surrounded by a cylindrical sleeve, forming an annular channel or conduit for the liquid. The conduit extends downwardly to the liquid reservoir at the bottom of the nebulizer. The reduced pressure of the gas jet exiting the stem draws the liquid upward through the channel to combine with the gas, the gas/liquid mixture passing through an orifice plate assembly and impinging upon a depending, rounded end or surface of a boss within the nebulizer. This abets the upcoming jet stream to nebulize any entrained liquid particles therein.

Incremental adjustment of the amount of nebulizer misting is obtained by varying the spacing between the upper end of the jet stem and a surrounding cylindrical step in the cylindrical sleeve to adjust the amount of liquid passing therebetween to be aspirated through the orifice plate, thus acting as a pinch valve.

The valve means for passage of fresh and exhaled air is also of a unique design, having a unitary valve flap divided into two oppositely-seated portions. One portion operates while the other remains seated, thus controlling each of the opposite air flows through the two manifold chambers.

Adjustment of the output of the nebulizer is effected through a rotatable top adjustment knob joined to a downwardly-extending valve shaft. The lower end of the shaft is ramped, and rests against the upper surface of a baffle plate assembly, controlling vertical positioning of the baffle and atomizer body and thus its spacing with respect to the top surface of the stem.

The upwardly extending tubular portion of the atomizer body has cut-away portions to allow the egress of the mist created within the volume defined by the atomizer body and the baffle plate. The aerosol mist then moves out of the nebulizer through the nebulizer outlet to mix with fresh air and travel through the upper manifold chamber to the user.

A further feature of the present invention is the utilization of the adjustment knob to effect filling and subsequent sealing of the unit. The adjustment knob is provided with a filling bore, which may be aligned with similar bores on the fixed cover of the nebulizer chamber and through a plate on the valve shaft. When so aligned, liquid may be added in the reservoir. When the knob is rotated to adjust the nebulization rate, the bores are placed out of alignment, sealing the reservoir.

Yet another feature of the invention is that its compactness results in a light nebulizer which is easily handled by a patient. This enables the lengthy hoses previously used for connecting a heavy manifold with the patient, to be shortened or eliminated. This in turn allows for delivery of more precise or accurate dosages to the patient, as less may be left in the transport path.

A further advantage is that, because of the efficient size of the medication chamber in the nebulizer, less medication is wasted, resulting in additional economies.

Another feature of the invention is that the precise valving of the nebulizer minimizes the amount of medication being recirculated in the nebulizer, and hence reduces frothing and foaming.

The openings at the ends of the manifold are formed in tubular members which permit the attachment of hoses or tubing should such be necessary for certain applications, or the direct attachment of a mouthpiece. The tubing at the outlet end of the manifold facilitates the attachment of standard biological filters.

A further advantage of the invention is that variable delivery rates provided by the nebulizer enable the physician to select the least uncomfortable delivery rate of irritating medicines. The rate of delivery can be reduced or increased to tolerable levels.

The designs of the component parts of the nebulizer are simple, facilitating easy manufacture and assembly. In fact, the parts are so simple that inexpensive injection molding techniques may be employed. The designs enable the use of materials such as polycarbonate, which lend a further advantage as being washable and rendering the unit reusable.

It should be appreciated that the compact design of the manifold further facilitates its ready shielding by lead to minimize the hazards extant in the use of radioactive pharmaceuticals. The compact design also saves on medicine as less medicine is wasted in the use of applicant's nebulizer. An additional facility enable loading of the nebulizer from the top through the adjustment knob, which further minimizes the loss of the pharmaceuticals.

BRIEF DESCRIPTION OF THE DRAWINGS

These and other objects, features and advantages of the invention will become apparent from a reading of the following specification when considered with the appended drawings, wherein:

FIG. 1 is a side view, partially cut away, of an aerosol delivery system constructed according to the invention having a standard biological filter at the manifold exhaust port;

FIG. 2 is a front view of the nebulizer of FIG. 1, showing the aerosol outlet port;

FIG. 3 is a cross-sectional view of the nebulizer of FIG. 2, taken along the section line 3—3;

FIG. 4 is an exploded perspective view of the nebulizer of FIGS. 3 and 4;

FIG. 5 is a detailed view in front elevation of the valve member; and

FIG. 6 is a side elevation view of the valve member.

DETAILED DESCRIPTION OF A PREFERRED EMBODIMENT OF THE INVENTION

As best shown in FIGS. 1, 2 and 3 of the drawings, a manifold, generally indicated by the numeral 10, includes a body 12 having tapered opposed first and second end portions 14 and 16 connected to tubes 18 and 20, respectively. Tubes 18 and 20 are of conventional or standard size facilitating the attachment of mouthpieces or hoses or a standard biological filter 22. Body 12 of the manifold is divided into upper and lower vertically juxtaposed chambers or compartments by a horizontal wall member 24 extending through the length of the body 12. The right hand end of the horizontal member 24 terminates at dual-acting valve 26.

Valve body 28 has two sets of openings 30 formed therethrough, permitting the passage of air in an inward direction into the upper chamber and in an outward direction from the lower chamber when flexible valve flap portions 32 and 34 respectively are deflected by fluid pressure differences across the valve. FIG. 1 shows the flap portion 32 being deflected inwardly upon the development of a lower than atmospheric pressure in the upper chamber due to inhalation activity by the patient, while at the same time flap 34 is maintained against the lower portion of the valve, thus preventing flow through the lower chamber. It is to be appreciated that flap 34 will be deflected outwardly, and flap 32 will be pressed against the valve body, upon a higher than atmospheric pressure in the chambers due to exhalation activity by the patient. Such dual action thus controls the flow of air through the device.

The left hand ends of the upper and lower chambers in the manifold are both open to the tube 18. Spent air simply does not flow into the upper chamber on exhalation because the valve flap 32 is closed. Likewise, exhaled air in the lower chamber does not flow back towards the patient on inhalation because the lower valve flap 34 is then closed. Rather, only medicated air in the upper chamber flows to the patient, such air being fresh air that entered the upper chamber on opening of the valve flap 32 and which has flowed past misting nebulizer 36.

The body 12 of the manifold 10 has nebulizer 36 mounted vertically generally midway of its length. As best seen in FIG. 1, the nebulizer extends through both the top and bottom of the body 12. The main body 38 of the nebulizer is tubular and of such size as to allow fresh air in the upper chamber to flow past it. The nebulizer extends downward through a receiving aperture in the horizontal member 24 and through the lower chamber, tapering to a reduced tubular portion 40 which rests against the lower portion of the manifold body. A gas inlet nozzle 42 projects from the nebulizer body and extends through the bottom of the manifold body for connection to a hose attached at its other end to a suitable supply of pressurized gas.

The front of the nebulizer, which faces the left end of the manifold as seen in FIG. 1, includes an outlet opening or port 44. The nebulizer is mounted in the manifold so that the port 44 is located on the downstream side of the upper chamber. Air entering the right hand end of the upper chamber of the manifold is mixed with the nebulized medication (mist) from the nebulizer and exits through the manifold outlet opening or tube 18 under the suction pressure of the patient during inhalation. The medicated air may be drawn into the patient either through a mouthpiece mounted directly on the tube 18 or through a hose terminating in such a mouthpiece (neither shown).

Figure 4:
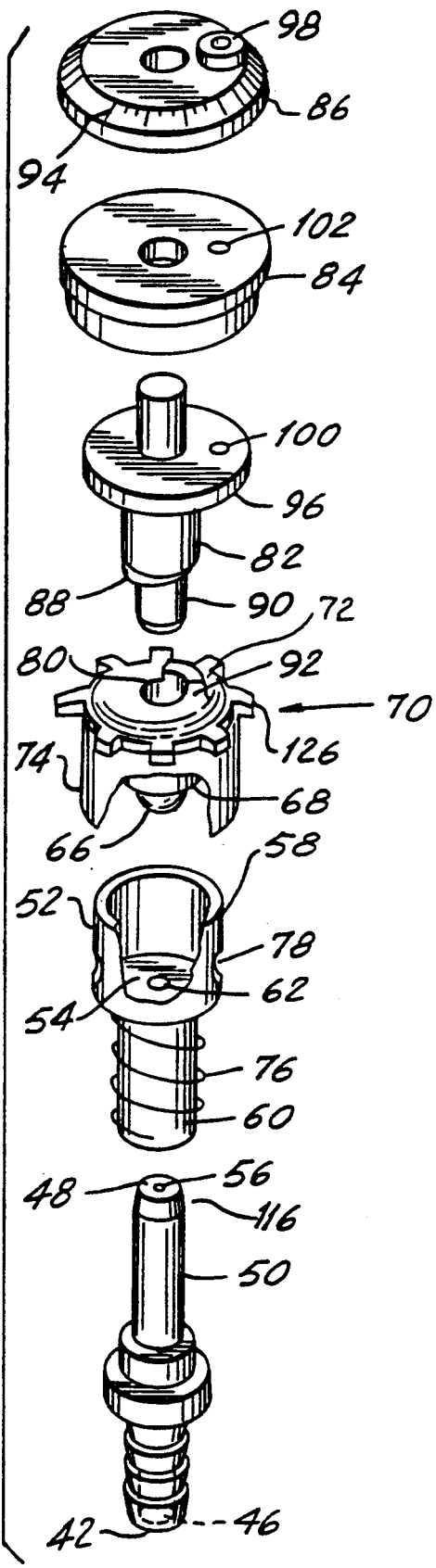
Figure 3:
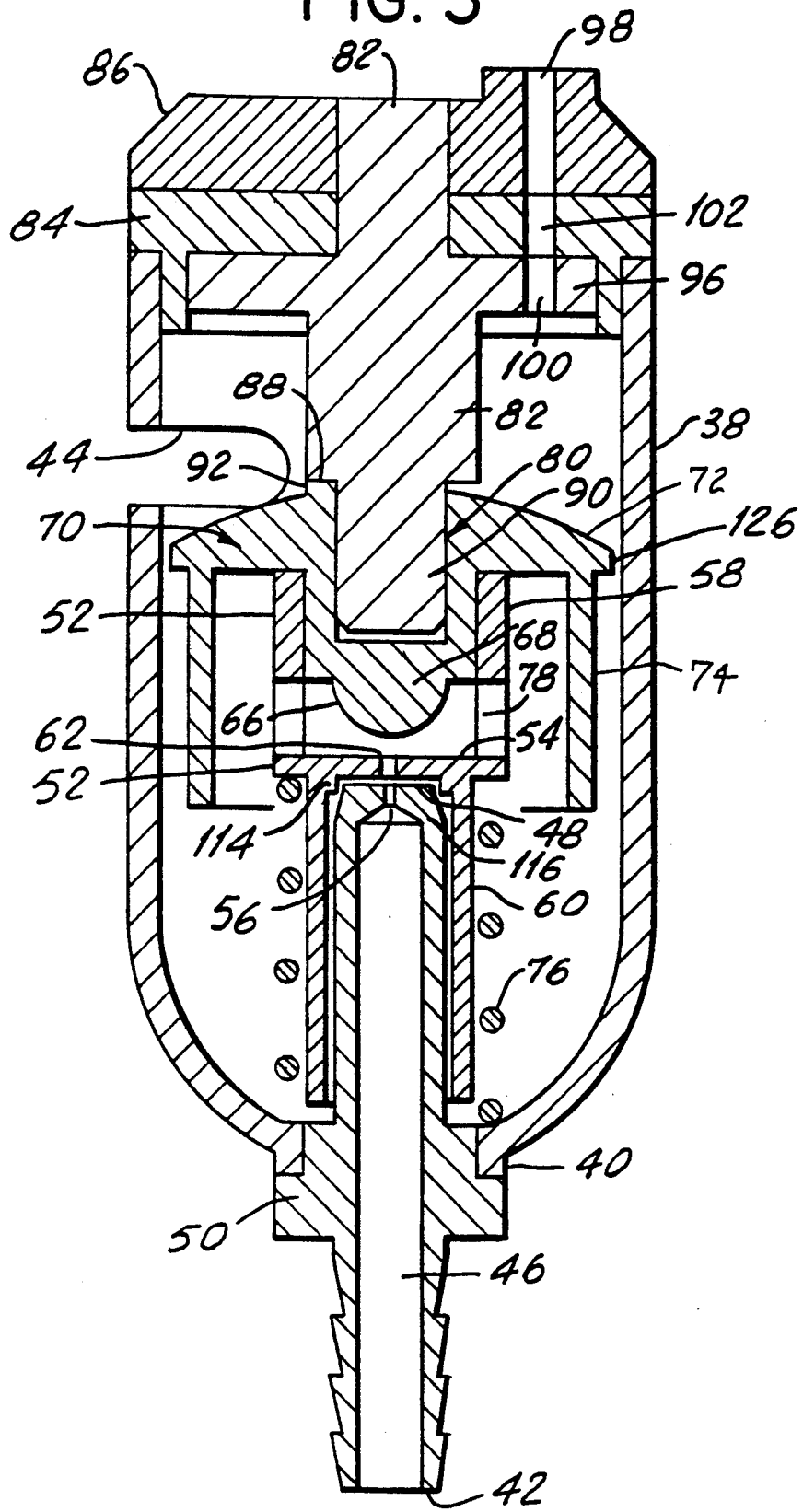

As best seen in FIGS. 3 and 4, the nebulizer 36 includes a passageway 46 through jet stem 50 for transmitting gas under pressure from the inlet nozzle 42 portion of the stem to the flat upper end surface 48 thereof, the stem being mounted to the lower end of the nebulizer main body and projecting upwardly within the body from the reduced tubular body portion 40 thereof. Stepped cylindrical orifice assembly 52 surrounds the stem, and includes an internal orifice plate 54 separating upper body portion 58 of the orifice assembly from lower portion 60. Lower portion 60 is cylindrical, and is dimensioned to fit upon stem 50 with a sliding fit thereon, the orifice 62 in orifice plate 54 being aligned with the restricted jet nozzle 56 of the stem passageway 46. The lower portion 60 extends downwardly to a point above the bottom of the nebulizer main body.

The orifice assembly 52 is urged upwardly, whereby orifice plate 54 is directed away from the upper end surface 48 of the jet stem to a spaced relationship with respect thereto, by a compression spring 76 encircling the depending lower tubular body portion 60 of the orifice assembly and engaging the step formed between the upper and lower body portions. The outer diameter of the jet stem 50 and the inner diameter of lower orifice assembly body portion 60 are such that an annular space exists therebetween, whereby a liquid in the bottom of the nebulizer can be drawn upwards in the annular space to flow laterally inward between the top surface 48 of the stem and the bottom surface of the orifice plate 54 by a lowered pressure condition at the jet nozzle 56 due to gas flow through the stem passageway 46, nozzle 56, and aligned orifice 62. The gas under pressure in the passageway 46 jets upwards through the layer of drawn liquid to entrain portions thereof, carrying such portions upwards through the orifice 62 to strike the rounded depending target surface 66 formed as the lower end of a boss 68 depending from baffle plate 70, further nebulizing or misting the entrained liquid portions.

Baffle plate 70 includes a generally circular body portion 72 from which boss 68 depends. The baffle plate's periphery is notched, whereby one or more of the keys The upper body portion 58 of orifice assembly 52 embraces the boss 68, and abuts against bottom surface of baffle plate body 72. The action of spring 76 maintains the orifice assembly in contact with the baffle plate body, whereby vertical travel of the baffle plate is transmitted to the orifice assembly. A coaxial, peripheral baffle wall 74 also depends from the baffle plate body 72. The lower end of the upper body portion 58 of the orifice assembly 52 has cut-away portions 78, best seen in FIG. 3, facilitating the exit of mist into the volume between the orifice assembly and the peripheral baffle wall 74. Assisted by the reduced pressure within the upper chamber due to the inhalation of the user, the aerosol mist then passes downward, around the lower end of the baffle wall, and up between the baffle wall and the outer housing of the nebulizer past the baffle plate through the notches therein to where it exits through port 44 into the upper chamber of the manifold for mixing with fresh air. Mist flow through the nebulizer and out through the port is further implemented by the gas flow through the nebulizer emanating from the jet stem 50.

The vertical relationship between the orifice plate 54 and the top surface 48 of jet stem 50 determines the amount of liquid subject to aspiration and nebulization. As seen in FIG. 3, the inner wall of orifice assembly lower body portion 60 has an internal peripheral step at its upper end, whereby shoulder 114 is developed, while the top or distal end 116 of jet stem 50 is slightly tapered, shown emphasized in FIG. 4. The annular spacing between the distal end of the stem and the shoulder 114 thus varies with the relative vertical positioning of the tapered portion of the stem and the shoulder, which together serve as a pinch valve assembly for the liquid in the annular space therebetween. Such spacing, and thus valve action, is controlled by the raising and lowering of the orifice assembly 52 by baffle plate assembly 70. In a preferred embodiment, the distal end 116 of jet stem 50 is beveled at a two-degree angle from the vertical. The jet orifice 56 is 0.018 inches in diameter, while the orifice 62 in orifice plate 54 is 0.030 inches in diameter. The inner diameter of the lower portion 60 of the orifice assembly may be 0.255 inches, while the diameter of jet stem 50 is 0.250 inches, providing an annular space therebetween of 0.0025 inches radius. To provide a full range of flow control, the step or shoulder 114 in the lower portion 60 should narrow the inner diameter to no more than 0.250 inches.

The elevation of the orifice assembly with respect to the jet stem is varied by operation of valve shaft 82, which is journaled for rotation about its vertical axis through nebulizer top piece 84 and which is provided with an adjustment knob 86. The lower portion of valve shaft 82 is provided with a step 88, the resulting downwardly-projecting cylindrical stub 90 being dimensioned to fit loosely within a bore 80 through the top surface of the baffle plate assembly 70. The step or shoulder 88 is ramped, while the baffle body 72 is provided with an upwardly-directed projection or follower 92. Rotation of the adjustment knob 86 and valve shaft 82 thus causes the ramp surface to slide against the follower, driving the baffle assembly, which is restrained from rotation by the engagement of the extended length of one of the keys 126 with the mating wall keyway, upward or downward, as the valve shaft is rotated, and thus varying the spacing between the tapered portion 116 of stem 50 and the shoulder 114 of orifice assembly 52. The outer surface of adjustment knob 86 may be provided with appropriate indicia 94, seen in FIG. 4, which allow the degree of spacing and thus the flow rate to be metered. It is contemplated that flow adjustment can be accomplished through a vertical travel, and thus ramp height, of approximately 0.02 inches.

In addition to providing flow adjustment, the combination of adjustment knob 86, top 84, and valve shaft 82 provide a novel means for allowing fill of the nebulizer. As best seen in FIGS. 3 and 4, adjustment knob 86 and intermediate disc-like ledge 96 of valve shaft 82 are provided with aligned transverse bores 98, 100, respectively. A similarly radially-positioned bore 102 is provided in top 84. When the adjustment knob and shaft are rotated as a unit to a point where their bores align with bore 102, medication can be loaded into the nebulizer to collect at the bottom reservoir end thereof. As the adjustment knob and valve shaft are turned for adjustment of jet flow, their associated bores move out of alignment with the bore 102 in top 84, thus closing the fill port mechanism. Preferably, the position of alignment for fill purposes is at an extreme end of rotation for the knob and shaft so as not to interfere with the normal range of adjustment for the device.

Figures 5, 6:
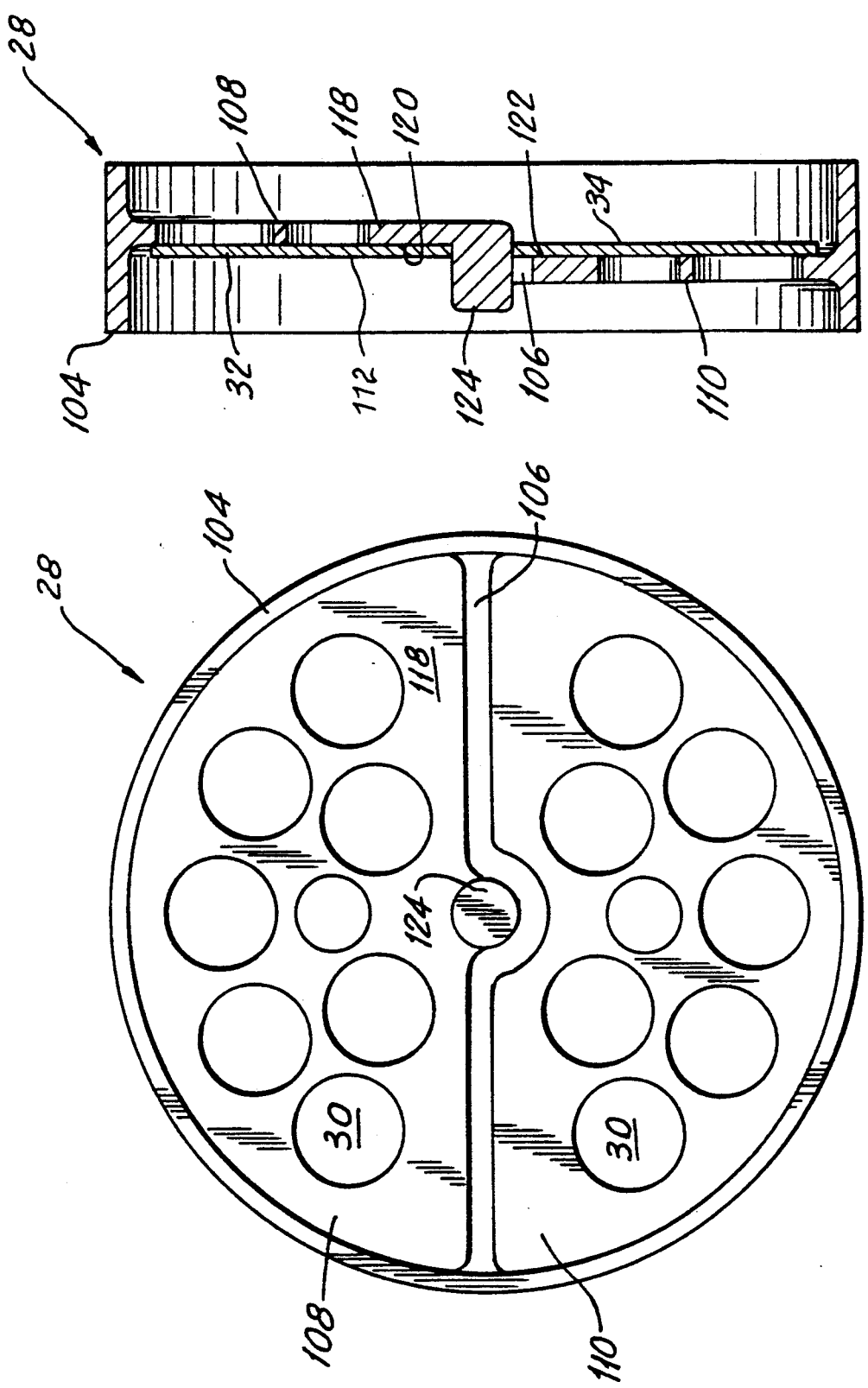

The valve assembly 26 represents a further advancement and improvement of the present invention. As detailed in FIGS. 5 and 6, the valve body 28 comprises a valve plate member 118 having apertures 30 surrounded by a peripheral hub 104 which is dimensioned to allow the valve body to be inserted within the manifold body 12 and be maintained in position therein in a frictional manner. The valve plate itself is divided into a pair of generally semicircular plate portions 108, 110, separated by transverse slot or space 106. The upper edge of lower portion 110, adjacent the slot 106, aligns with manifold body divider 24 when installed in the manifold body 12 such that the semicircular portions 108, 110 are associated with the upper and lower manifold chambers, respectively. As best seen in FIG. 6, the semicircular plate portions 108, 110 are offset from each other to permit the utilization of a single flat, flexible element 112 to define flap elements 32 and 34. The portion of the flexible element 112 defining flap 32 rests against front face 120 of plate portion 108, while the portion of flexible element 112 defining flap 34 rests against rear face 122 of plate portion 110 to close off the openings 30. The flexible element may preferably be silicone rubber of 0.018 inch thickness. The slot 106 allows the flexible element 112 to be inserted against the opposed faces, projecting central nub 124 formed at the lower edge of semicircular plate portion 108 and extending outwardly therefrom allowing the flexible element, which is provided with a mating central aperture, to be mounted thereon and retained against the plate portion faces. The manifold body divider 24 may be provided with an appropriate notch to accept the hub.

In use, medication is inserted into the nebulizer 32 via the fill opening 98. Gas under pressure is then admitted to the passageway 46. The patient inhales, causing air to enter the upper chamber past the check valve flap 32. The pressurized gas in the passageway 42 jets upwards, entraining the liquid medication that has moved by aspiration to the vicinity of the jet orifice 56, the gas and liquid passing upwardly through orifice 62 in the orifice plate 54 to strike against the rounded impact surface 66 of the boss 68 to fully aerosolize the liquid medication. The resulting mist created flows outward through the cut-away portions 78 in the orifice assembly, downwards between the orifice assembly and the baffle wall 74, then upwards between the baffle wall and the housing of the nebulizer 36 to exit through the output port 44. The air/aerosol mixture continues through the upper chamber of the manifold under the influence of the patient's inspiratory breath and exits to the patient through the output port in the upper manifold tube 18.

If the mixture being absorbed by the patient was uncomfortable or of an inappropriate strength, suitable turning would be made of the adjustment knob 86 on the nebulizer to vary the spacing between the stem upper surface 48 and the underside of the orifice plate to change the rate of medication aspiration.

While applicant has shown and described a preferred embodiment of the invention, it will be apparent to those skilled in the art that other embodiments utilizing principles of the invention can be readily fabricated. Accordingly, it is intended to be limited only by the scope or spirit of the appended claims.

I claim:

1. Apparatus for providing a nebulized fluid to a user, comprising a tubular body having an ambient air inlet at a first end and a mouthpiece outlet at a second end, a transverse horizontal divider extending substantially along the length of said tubular body dividing said body into first and second parallel passageways; valve means mounted at an end of said divider and having a unitary valve flap for providing independent one-way air flow inwardly into said tubular body from said inlet end through said first parallel passageway and outwardly from said tubular body from said second parallel passageway through said inlet; a nebulizer having a body extending transversely through said first and second passageways and having an adjustment means for controlling fluid flow rate extending upwardly from said body and a gas inlet extending downwardly from said body; said nebulizer body having a nebulized-liquid output port located within said first parallel passageway oriented towards said second end.

2. The apparatus of claim 1, wherein said nebulizer includes a top affixed to said nebulizer body, said adjustment means comprising a knob located above and adjacent said top, said top and adjustment knob each having an aperture; and means for permitting rotation of said adjustment knob to and from a position wherein said apertures are aligned to allow liquid to be nebulized to be loaded into the body of said nebulizer.

3. The apparatus of claim 2 further comprising a shaft coupled to said adjustment knob for rotation therewith, said shaft having a plate mounted thereon with an aperture therethrough in alignment with said aperture in said adjustment knob.

4. The apparatus of claim 3 further comprising a hub projecting outwardly from said first valve plate portion proximate the edge thereof, said flap having an aperture adapted to accept said hub therethrough.

5. The apparatus of claim 1, wherein said nebulizer includes a hollow stem extending upwardly within said body from said gas inlet and having a gas nozzle at its upper end; a cylindrical orifice assembly surrounding an upper portion of said stem whereby an annular fluid flow channel is defined between said orifice assembly and said stem; and co-acting valve means on said stem and orifice assembly connected to said adjustment means responsive to a relative longitudinal relationship between said stem and orifice assembly to control the passage of fluid through said annular fluid channel.

6. The apparatus of claim 5, wherein said co-acting valve means comprise a tapered portion of said stem and an internal step portion of said orifice assembly.

7. The apparatus of claim 6, wherein said tapered portion of said stem is proximate said upper end of said stem.

8. The apparatus of claim 6, further comprising an intermediate drive element coupled between said adjustment means and said stem and orifice assembly.

9. The apparatus of claim 8, wherein said drive element is coupled to a baffle plate assembly.

10. The apparatus of claim 8, wherein said drive element comprises a shaft having a cam surface and a cam follower operatively connected to said orifice assembly.

11. The apparatus of claim 10 further comprising a spring mounted to said orifice assembly to bias said follower against said cam surface.

12. The apparatus of claim 11 further comprising a baffle plate mounted upon said orifice assembly, said baffle plate bearing said cam follower.

13. The apparatus of claim 10 further comprising a baffle plate assembly mounted for vertical travel within said nebulizer body adjoining said orifice assembly, said baffle plate assembly bearing said cam follower.

14. The apparatus of claim 13, wherein said baffle plate assembly includes a target surface positioned above said gas nozzle.

15. The apparatus of claim 1, wherein said valve comprises a hollow valve body defining a passageway therethrough; first and second perforated valve plate portions each having front and rear faces, extending substantially across an opposed portion of said passageway, said first and second valve plates being offset from each other such that the front face of said first valve plate portion is rearward of the rear face of said second valve plate, said first and second valve plates each having an adjacent edge extending across said passageway defining a space therebetween; said unitary flap being mounted against said front face of said first valve plate portion and the rear face of said second valve plate portion, said valve body being mounted within said tubular body whereby the edge of said second valve plate is aligned with said transverse divider.

* * * * *